United States Patent [19]

Govil et al.

[11] Patent Number: 4,908,213
[45] Date of Patent: Mar. 13, 1990

[54] TRANSDERMAL DELIVERY OF NICOTINE

[75] Inventors: Sharad K. Govil, Plantation; Paul Kohlman, Deerfield Beach, both of Fla.

[73] Assignee: Schering Corporation, Kenilworth, N.J.

[21] Appl. No.: 313,103

[22] Filed: Feb. 21, 1989

[51] Int. Cl.$^4$ .......................... A61L 15/00; A61B 5/00
[52] U.S. Cl. .................................... 424/447; 424/449; 128/156
[58] Field of Search ................ 424/422–426, 424/447, 448, 449; 128/156

[56] References Cited

U.S. PATENT DOCUMENTS 4,597,961  7/1986  Etscorn .............................. 424/448
4,839,174  6/1989  Baker et al. ........................ 424/447

FOREIGN PATENT DOCUMENTS 3438284  3/1985  Fed. Rep. of Germany .
8801516  3/1988  PCT Int'l Appl. .

OTHER PUBLICATIONS

Rose, et al., Clin. Pharmacol. Ther., 38, 4, (1985), pp. 450–456.
CA102:1911882 (1985).

Primary Examiner—Nancy A. B. Swisher
Attorney, Agent, or Firm—Anita W. Magatti; James R. Nelson; Stephen I. Miller

[57] ABSTRACT

A transdermal nicotine patch comprising an antipruritic to counteract pruritis observed with the transdermal administration of nicotine is disclosed. The patch can be any conventional patch type, e.g., reservoir, adhesive or polymeric matrix.

14 Claims, 1 Drawing Sheet

4,908,213

TRANSDERMAL DELIVERY OF NICOTINE

BACKGROUND OF THE INVENTION

This invention relates to a transdermal drug delivery patch, in particular, a patch useful for the transdermal delivery of nicotine. The patch is useful in that it delivers an amount of nicotine which achieves a physiological effect, curbing the urge to smoke tobacco, and thus easing the physiological symptoms of nicotine withdrawal.

A long felt need has existed in the medical art for a transdermal nicotine patch. In the past, nicotine has been administered orally, for example by chewing a resin gum containing nicotine such as that sold commercially under the trade name NICORETTE.

Several transdermal nicotine products have recently been disclosed. One such transdermal delivery device is disclosed by Lohmann & Co. GmbH in WO 8801-516A, filed Aug. 28, 1986. Lohmann describes a controlled release transdermal delivery system with an active substance, e.g., nicotine, in a depot formed by a reservoir contained between an adhesive layer and a backing layer. A dispersion device is connected to the depot which is spatially defined from the matrix.

Von Tilly, Ger. Offen. DE No. 3,438,284 similarly discloses a nicotine-reservoir containing transdermal preparation which is alleged to deliver approximately 20 to 30 mg/day from a 10/20 cm$^2$ patch.

Rose, et al. "Transdermal nicotine reduces cigarette craving and nicotine preference", *Clin. Pharmacol. Ther.*, Vol. 38, No. 4, pp 450-456 (Oct., 1985) discloses that transdermal nicotine base (8 mg) applied in 30 percent aqueous solution under a polyethylene patch was helpful in reducing the urge to smoke tobacco.

It has been determined that a relatively constant nicotine blood level may help to curb the urge to smoke. Hence, one objective of the invention is to provide a transdermal nicotine patch which will deliver nicotine transdermally over an extended period of time, e.g., 16 to 24 hours. A further objective is to provide a transdermal nicotine patch which causes a minimum of local pruritis or discomfort where applied and worn on the skin.

These objectives, as well as others, will become more readily apparent from the following detailed description taken in conjunction with the drawings wherein.

Figure 1:
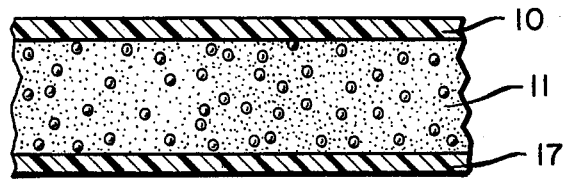
FIG. 1 is a cross-sectional schematic view of a transdermal nicotine patch in an adhesive matrix form.

During testing of the transdermal nicotine patch described herein, it was discovered that nicotine delivered transdermally causes severe pruritis with practically no local erythema or inflammation. This pruritic reaction appears to be a pharmacological response to nicotine rather than a component of a general inflammatory reaction, since little if any erythema or inflammation are observed.

SUMMARY OF THE INVENTION

A transdermal nicotine patch is disclosed, comprising (a) an amount of nicotine or a salt or solvate thereof effective for treating the symptoms associated with tobacco smoking cessation, said nicotine to be transdermally delivered to a patient in need of such treatment and (b) an effective amount of a topical antipruritic. A preferred antipruritic is bisabolol, in an amount ranging from about 0.10 to about 2 percent of the total weight of the nicotine, antipruritic and carrier.

The transdermal patch may comprise an adhesive matrix, a reservoir or a polymeric matrix for containing the nicotine and/or antipruritic, and the transdermal patch preferably further comprises an easily removed release liner to protect the patch prior to application, and may further comprise a rate-limiting membrane.

The invention further includes a method of treating the urge to smoke tobacco and/or nicotine withdrawal, which method comprises transdermally delivering to a patient in need of such treatment an effective amount of nicotine in combination with the topical or transdermal use of an antipruritic such as bisabolol.

DETAILED DESCRIPTION

The invention described herein involves in its preferred embodiment the incorporation in a transdermal device for administering nicotine and at least one antipruritic compound useful for reducing or eliminating itching caused by the transdermal penetration of nicotine.

The active ingredient in the patch described herein is nicotine or a pharmacologically and pharmaceutically acceptable salt or solvate thereof. Typical salts and solvates include the hydrochloride, dihydrochloride, sulfate, tartrate, bitartarate, zinc chloride double salt monohydrate and salicylate. The concentration of nicotine in the patch generally ranges from about 5 to about 40 percent of the total weight of the nicotine, antipruritic and carrier (e.g., the weight of the adhesive matrix, the polymeric matrix or the contents of the reservoir, but not including the weight of the backing material, release liner or rate controlling membrane) on a (w/w) basis. The preferred active ingredient is nicotine free base, and the preferred concentration of active ingredient is about 10 to about 20%.

The antipruritic used in the transdermal nicotine patch is included to counter the pruritic effects experienced when delivering nicotine transdermally. As such, it is referred to herein as the antipruritic, rather than as the "active ingredient" even though it is clearly "active" in the sense that it reduces itching. The antipruritic is without pharmacological effect with respect to the nicotine withdrawal symptoms that are being treated.

One such preferred antipruritic compound is bisabolol, also known as 2-(4-methyl-3-cyclohexenyl)-6-methyl-5-hepten-2-ol, and more preferably α(−)bisabolol. Such a compound has not previously been used to effectuate the transdermal delivery of drugs, and in particular, nicotine, although it has been used as a cosmetic adjuvant. It is commercially available from BASF Wyandotte Corp., Parsippany, N.J. α(−)bisabolol is present in an amount ranging from about 0.10 to about 2%, more preferably about 0.1 to about 1% of the total weight of the nicotine, antipruritic and carrier.

Examples of topical antipruritics effective in reducing itching during transdermal nicotine delivery other than bisabolol, mentioned above, are oil of chamomile, chamazulene, allantoin, D-panthenol glycyrrhetenic acid, corticosteroids, antihistamines, and combinations thereof. ANTIPHLOGISTICUM "ARO", commercially available from Novarom GmbH, Holzminder, Germany, comprising a combination of 18-β-glycyrrhetenic acid and D-panthenol, is a particularly useful combination.

Other ingredients useful in preparing the carrier for the transdermal nicotine patches described herein include conventional adhesives, solvents, co-solvents, plasticizers, polymeric matrices, stabilizers, thickeners, preservatives, etc.

Examples of pharmaceutically acceptable pressure sensitive adhesives useful in delivery devices for nicotine include acrylic, silicone, vinyl acetate and synthetic or natural rubber adhesives as well as other adhesives useful in transdermal drug delivery. The adhesives may be used alone or in combination to prepare an adhesive drug matrix or may be applied to the skin-contacting surface of a polymeric matrix or reservoir patch to adhere said patch to the skin. Examples of adhesives are acrylic adhesives such as RA 2484, RA 2333, RA 2397, R 363 and R 362 from Monsanto Co. Other acrylic adhesives, such as Durotak, manufactured by Morton Thiokol, Inc., and Neocryl XA5210bby Polyvinyl Chemicals, Ltd. may be utilized. Vinyl acetate adhesives include Flexcryl-1614, 1617, 1618 and 1625 from Air Products. Numerous silicone based adhesives may be used, such as Q72929, Q27406, X72920 and 355, each manufactured by Dow-Corning. Natural and synthetic rubbers include polyisobutylenes, neoprenes, polybutadienes and polyisoprenes.

Polymeric matrix-forming agents include pharmaceutically acceptable polymers such as polyvinyl alcohol, polyvinylpyrrolidones, gelatin and partially hydrolyzed polyvinyl alcohols.

Examples of solvents useful for effecting the transdermal delivery of nicotine include aqueous and organic solvents. As used herein the term solvent differs from the term co-solvent only in the most general sense. A co-solvent is a liquid which generally is a non-solvent, in which the active ingredient becomes soluble upon the addition of a small amount of a true solvent. Water is a typical solvent used in the transdermal nicotine patch. Polar organic solvents, such as ethanol, may also be useful.

Co-solvents useful in the transdermal nicotine patch include, for example, mineral oil, silicone-based liquids, and low molecular weight polyisobutylenes.

Suitable preservatives, antioxidants and chelating agents can be included in the transdermal nicotine patch, such as butylated hydroxyanisole (BHA), butylated hydroxytoluene (BHT), sodium metabisulfate, a-tocopherol, maleic acid, ethylenediaminetetraacetic acid (EDTA), and cysteine hydrochloride.

Components useful for imparting the desired wear and pharmacokinetic characteristics to the transdermal nicotine patch include, for example, polymeric matrix-forming materials added to facilitate curing of the adhesives, for example Aerotex Resin 3730 (American Cyanamid) and a thickener may be added to adjust the viscosity of the polymer mixture to the desired viscosity for coating on a backing material. The thickener can be an acrylic polymer thickener such as AMSCO 6038A (Unocal), methyl cellulose and hydroxypropylmethyl cellulose. Plasticizers may be added to impart softness and flexibility to the adhesive, a typical plasticizer being glycerin. Stabiliziers, added to prevent degradation by heat and light and to improve aging characteristics, include polyvinylpyrolidone. Examples of formulations are shown below in Table 1. Formulae 1–3 are adhesive formulations, Formula 4 is a reservoir formulation, and Formula 5 is a polymeric matrix formulation.

TABLE 1

| INGREDIENT | FUNCTION | EXAMPLES OF FORMULATIONS | | | | |
| --- | --- | --- | --- | --- | --- | --- |
| | | FORMULA 1 | FORMULA 2 | FORMULA 3 | FORMULA 4 | FORMULA 5 |
| Acrylic Pressure Sensitive Adhesive | Adhesive | 71.5% | — | — | — | — |
| Silicone Pressure Sensitive Adhesive | Adhesive | — | 52.5% | — | — | — |
| Polyisobutylene Pressure Sensitive Adhesive | Adhesive | — | — | 87% | — | — |
| Mineral Oil | Co-solvent | — | — | — | 12.45% | — |
| Silicone Medical Fluid | Co-solvent | — | — | — | 80% | — |
| Glycerin | Plasticizer | — | — | — | — | 11.5% |
| Polyvinyl Alcohol | Polymeric matrix | — | — | — | — | 25.3% |
| Polyvinylpyrrolidone | Stabilizer | — | — | — | — | 3.1% |
| Nicotine Free Base | Active Drug | 20% | 40% | 10% | 5% | 30% |
| Water | Solvent | 4% | — | — | — | 17.6% |
| Butylated Hydroxyanisole | Anti-oxidant | 2.5% | 2.5% | 2.5% | 2.5% | 2.5% |
| α(-)Bisabolol | Anti-pruritic | 1% | 5% | 0.5% | 0.5% | 10% |
| Acrylic Polymer Thickener | Thickener | 1% | — | — | — | — |
| | | 100% | 100% | 100% | 100% | 100% |

The transdermal nicotine patch described herein can be in any conventional patch form, such as a polymeric matrix type, a reservoir type or an adhesive type, with the adhesive type being preferred.

As shown in each of the Figures, an impermeable backing layer 10 is typically included to render the contents of the patch impervious to the outside environment during use. Suitable components for use as an impermeable backing material include such materials as foam, metal foil, polyester, low density polyethylene, copolymers of vinyl chloride and polyvinylidene chloride (e.g. Saran), and laminates thereof. A preferred backing material is a metallized plastic such as metallized polypropylene.

A protective release liner 17, also shown in each of the figures, is typically included. The release liner is removed prior to application and use; it is typically present to protect the patch, e.g. by preventing dirt from sticking to the patch adhesive during shipment and storage. Examples of materials suitable for release liners are polyethylene and polyethylene-coated paper, preferably silicon-coated to facilitate removal.

The patch shown in cross-section in FIG. 1 exemplifies an adhesive/nicotine/antipruritic combination 11 applied to the backing layer during manufacture. The combination 11 may also include therein other components such as a polymeric matrix-forming material.

Figure 2:
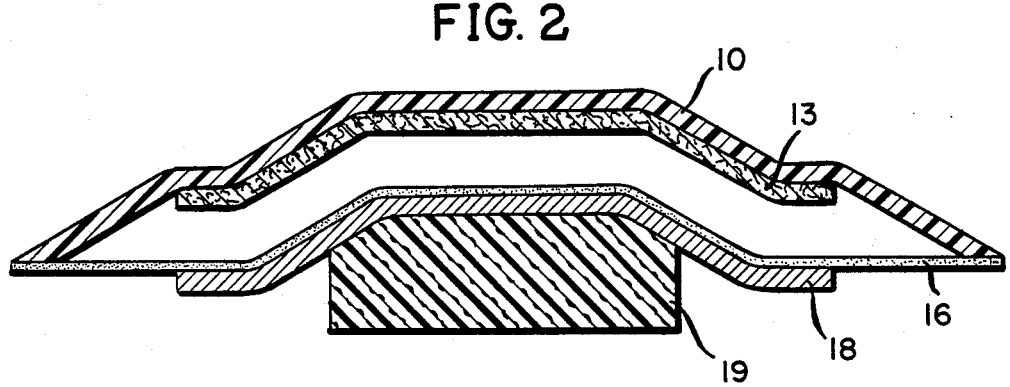
FIG. 2 is a cross-sectional view of an alternative embodiment of a transdermal nicotine patch, i.e., a polymeric matrix patch.

The patch exemplified in FIG. 2 illustrates elements of a matrix-type patch, wherein distinct portions of the patch contain the active ingredient and the adhesive; the matrix 19 comprises the nicotine or salt or solvate thereof and an antipruritic compound, which is separated from the backing layer 10 by a paper foil baseplate 18 and an absorbant pad 13. The baseplate 18 prevents the migration of the active into the absorbant pad 13, while the pad absorbs moisture from the adhesive, which in turn absorbs moisture from the skin. The adhesive 16 is peripheral to the matrix and keeps the matrix in contact with the skin surface. The patch preferably also comprises a release liner covering the adhesive, the drug matrix and the baseplate.

Figure 3:
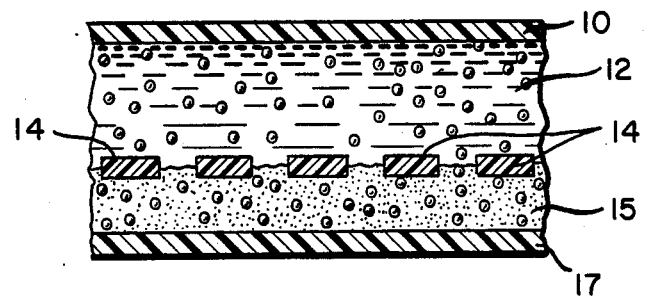
FIG. 3 is a cross-sectional view of a second alternative embodiment of a transdermal nicotine patch, i.e., a reservoir patch.

FIG. 3 shows a cross-section of a reservoir type patch wherein a reservoir 12 is formed, which reservoir contains the nicotine/antipruritic combination and may also contain one or more additional components such as preservatives or thickeners. A rate-controlling membrane 14 may be included to effect controlled release of the nicotine/antipruritic from the patch. Alternatively, the nicotine may be contained in a distinct section of the patch such as reservoir 12, and the antipruritic may be contained in a separate layer 15 when it is not desirable to mix the two components.

Materials suitable for rate-controlling membranes include ethylene-vinyl acetate (EVA) copolymer membranes (e.g. 1–20% vinyl acetate), polyvinylalcohol (PVA) gels and silicone films.

The adhesive, polymeric and reservoir patches are all made by methods well known in the art.

The transdermal nicotine patch is used by simply removing the protective layer to expose the adhesive surface, and applying the patch to the skin of a patient in need of such treatment so that the patch adheres to the skin.

Transdermal delivery of an effective amount of nicotine thereby occurs over an extended period of time. The patch described herein provides adequate serum levels of nicotine which are useful for a period of from about 4 to about 24 hours, after which the patch is replaced. Preferably the patch is used for about 12 to 24 hours and then replaced.

Effectiveness of the antipruritic in the transdermal nicotine patch is measured in terms of reduced itching as noted from the data below in Table 2. An adhesive-type transdermal nicotine patch comprising nicotine and bisabolol was used to test itching in patients. The concentration of antipruritic and nicotine was varied, and the number of patients complaining of itching was evaluated, along with the severity of the itching experienced.

TABLE 2

| Control Patch % Nicotine | % α(−)Bisabolol | Number Tested | Adverse Reactions (i.e. Itching) | Number of Severe Reactions Requiring Removal of Patch |
|---|---|---|---|---|
| 40% | 0 | 12 | 12/12[a] | 12 |
| 20% | 0 | 12 | 5/12[a] | 1 |
| 10% | 0 | 12 | 7/12[a] | 0 |
| Test Patches | | | | |
| 20% | 5% | 12 | 7/12 | 1 |
| 20% | 10% | 12 | 7/12 | 1 |
| 20% | 0.5% | 12 | 4/12[b] | 0 |
| 20% | 1% | 12 | 6/12[b] | 0 |
| 10% | 10% | 12 | 5/12 | 1 |
| 10% | 5% | 12 | 4/12 | 0 |

Notes
[a]Itch duration was long, until the patch was removed.
[b]Itch duration in those experiencing side effects was generally low, not longer than 10 minutes.

As is seen from Table 2 above, the formulations containing 0.5 to 1 percent α(−)bisabolol caused fewer itching side effects than those without the antipruritic, and also fewer side effects than those patches which contain 5 to 10 percent of the antipruritic. Additionally, severity of the itching side effect is greatly reduced in the formulations containing 0.5 to 1 percent antipruritic. Hence it is concluded that a transdermal nicotine patch containing α(−)bisabolol is effective in treating nicotine withdrawal symptoms with a minimum of adverse itching side effects.

While certain specific embodiments of the transdermal nicotine patch have been described herein, numerous modifications are possible and within the scope of the invention. Consequently, interpretation of the claims is not to be limited thereby.

We claim:

1. An adhesive, polymeric matrix or reservoir transdermal delivery patch for the controlled release of nicotine comprising an amount of nicotine or a pharmaceutically acceptable salt or solvate thereof effective to treat symptoms associated with tobacco smoking cessation and an amount of an antipruritic effective to treat the pruritis associated with transdermal delivery of nicotine, in a pharmaceutically acceptable carrier.

2. A transdermal patch of claim 1 wherein the salts and solvates of nicotine are selected from the group consisting of the hydrochloride, dihydrochloride, sulfate, tartrate, bitartarate, zinc chloride double salt monohydrate and salicylate.

3. A transdermal patch of claim 1 wherein the nicotine or salt or solvate thereof comprises 5 to 40% of the total weight of the nicotine or salt or solvate thereof, antipruritic and carrier.

4. A transdermal patch of claim 3 comprising nicotine free base.

5. A transdermal patch of claim 4 wherein the antipruritic is selected from the group consisting of bisabolol, oil of chamomile, chamazulene, allantoin, D-panthenol, glycyrrhetenic acid, corticosteroids and antihistamines.

6. A transdermal patch of claim 5 wherein the antipruritic is bisabolol.

7. A transdermal patch of claim 6 wherein the antipruritic is α(−)bisabolol.

8. A transdermal patch of claim 7 wherein the α(−)bisabolol comprises about 0.1 to about 2% of the total weight of the nicotine or salt or solvate thereof, α(−)bisabolol and carrier.

9. A transdermal patch of claim 8 wherein the carrier comprises a pharmaceutically acceptable pressure sensitive adhesive.

10. A transdermal patch of claim 9 wherein the adhesive is selected from the group consisting of acrylic, silicone and polyisobutylene adhesive.

11. A transdermal patch of claim 8 wherein the carrier comprises a polymeric-matrix forming agent.

12. A method for treating the symptoms associated with tobacco smoking cessation comprising applying a transdermal patch of claim 8 to the skin of a human in need of such treatment.

13. An adhesive transdermal patch of claim 1 comprising 20% nicotine free base and 1% α(−)bisabolol, and wherein the carrier comprises 71.5% acrylic pressure sensitive adhesive, 4% water, 2.5% butylated hydroxyanisole and 1% acrylic polymer thickener.

14. A method for treating the symptoms associated with tobacco smoking cessation comprising applying a transdermal patch of claim 1 to the skin of a human in need of such treatment.

* * * * *